United States Patent [19]

Naruse et al.

[11] Patent Number: 4,761,510

[45] Date of Patent: Aug. 2, 1988

[54] SELECTIVE PREPARATION OF TRANS-PERHYDROACENAPHTHENE

[75] Inventors: Yoshihiro Naruse; Toshihide Suzuki, both of Chiba, Japan

[73] Assignee: Kawasaki Steel Corporation, Kobe, Japan

[21] Appl. No.: 45,580

[22] Filed: May 4, 1987

[30] Foreign Application Priority Data

May 12, 1986 [JP] Japan ................................. 61-107970

[51] Int. Cl.$^4$ ................................................ C07C 5/03
[52] U.S. Cl. ...................................... 585/268; 585/270
[58] Field of Search ................................. 585/268, 270

[56] References Cited

U.S. PATENT DOCUMENTS

| | | | |
|---|---|---|---|
| 3,128,316 | 4/1964 | Schneider | 585/352 |
| 3,859,370 | 1/1975 | Carter et al. | 585/270 |
| 3,997,617 | 12/1976 | Hosler et al. | 585/268 |
| 4,041,086 | 8/1977 | Moore et al. | 570/130 |

FOREIGN PATENT DOCUMENTS 0164038  12/1985  European Pat. Off. .

OTHER PUBLICATIONS

"Preparation of Diamondoid Hydrocarbons by Rearrangement Employing a Chlorinated Platinum-Alumina Catalyst", *Journal of the American Chemical Society*, by D. E. Johnston et al., Jun. 2, 1971, pp. 2798 and 2799.

*Primary Examiner*—Curtis R. Davis
*Attorney, Agent, or Firm*—Young & Thompson

[57] ABSTRACT

Trans-isomers of perhydroacenaphthene are selectively prepared through hydrogenation of acenaphthene by effecting hydrogenation at 200° to 300° C. in the presence of a nickel catalyst on a kieselguhr carrier.

5 Claims, 1 Drawing Sheet ated acenaphthene, characterized by effecting the hydrogenation reaction at a temperature of 200° to 300° C. in the presence of a catalyst comprising nickel carried on kieselguhr, producing trans-isomers as a major product.

SELECTIVE PREPARATION OF TRANS-PERHYDROACENAPHTHENE

BACKGROUND OF THE INVENTION

This invention relates to the preparation of perhydroacenaphthene useful as a high boiling oil by hydrogenating acenaphthene. More particularly, it relates to a process for selectively preparing trans-perhydroacenaphthene in pure form rather than as a mixture of isomers, which can be subsequently used as an intermediate for such chemical reactions as synthesis of adamantanes without incurring any difference in reaction route, activation energy, and reaction yield.

It is well known in the art to hydrogenate a polycyclic aromatic compound in an atmosphere of pressurized hydrogen in the presence of a noble metal-based catalyst such as Pt and Pd catalysts or a nickel-based catalyst such as Raney nickel and nickel/kieselguhr catalysts to eventually produce a corresponding perhydro compound.

For acenaphthene, it is well known that by hydrogenating acenaphthene in the presence of a Raney nickel catalyst, perhydroacenaphthene is produced by way of tetrahydroacenaphthene. As described in the literature (see J. Am. Chem. Soc., June 2, 1971, 2798), four stereoisomers are known for perhydroacenaphthene. The detail of these four isomers has not been generally investigated and no attempt has been made to selectively synthesize a particular isomer. Consequently, perhydroacenaphthene is usually available as a mixture of four isomers. It has never been attempted to selectively synthesize a particular isomer or a particular group of isomers.

No problem is encountered with an isomer mixture when perhydroacenaphthene is merely used as a high-boiling oil. It is, however, desirable to selectively synthesize a particular isomer or a particular group of isomers in using perhydroacenaphthene as an intermediate for chemical reaction to a final product because the reaction route and the activation energy involved in the reaction vary with isomers, resulting in varying reaction yields. As regards the literature and patent publications, no such concept about perhydroacenaphthene has been reported.

The Raney nickel used for hydrogenation requires a solvent for certain starting materials and is inconvenient because of its short life and the careful handling thereof that must be observed.

SUMMARY OF THE INVENTION

An object of the present invention is to provide a novel process for selectively preparing perhydroacenaphthene in high yields.

Another object of the present invention is to provide a novel process for selectively preparing a particular isomer of perhydroacenaphthene, especially two trans-isomers as a main product.

Perhydroacenaphthene is useful as an intermediate for the synthesis of medical compounds. We have discovered that in producing perhydroacenaphthene for such destination by hydrogenating acenaphthene in the presence of various hydrogenating catalysts, the ratio of the four isomers of perhydroacenaphthene produced can be controlled to a significant extent by a choice of the catalyst and reaction conditions.

According to the present invention, there is provided a process for selectively preparing trans-perhydroacenaphthene by hydrogenating acenaphthene, characterized by effecting the hydrogenation reaction at a temperature of 200° to 300° C. in the presence of a catalyst comprising nickel carried on kieselguhr, producing trans-isomers as a major product.

BRIEF DESCRIPTION OF THE DRAWING

The invention will be more fully understood by reading the following detailed description taken in conjunction with the accompanying drawing, in which.

the only FIGURE.

DETAILED DESCRIPTION OF THE INVENTION

Figure 1:
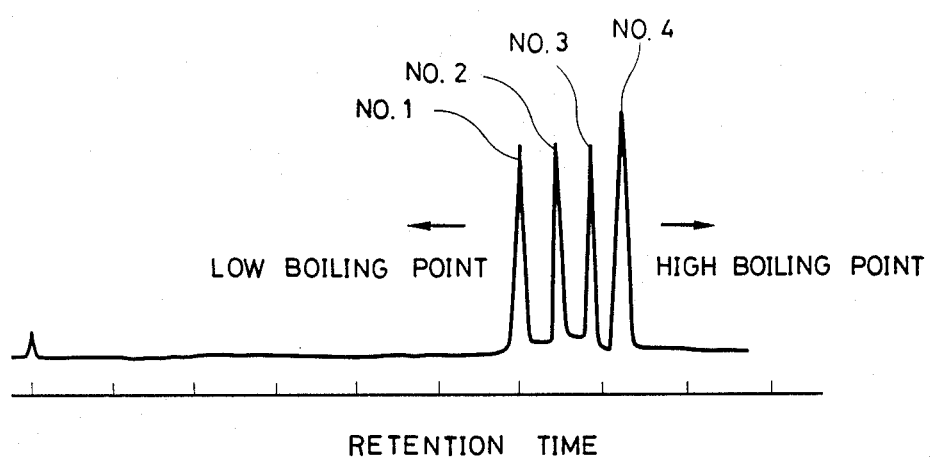
FIG. 1 is a gas chromatogram of a mixture of four isomers of perhydroacenaphthene.

Hydrogenation reaction of acenaphthene proceeds as follows.

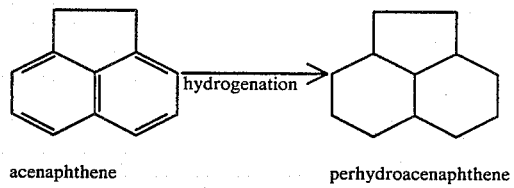

acenaphthene           perhydroacenaphthene

Four isomers are involved in perhydroacenaphthene. The isomers can be identified by, for example, the analysis chart obtained by gas chromatography using a packing material of the nature allowing materials to elute in the order of their boiling point. Based on a series of analysis results, it is supposed that peak Nos. 1 and 3 in FIG. 1 are attributable to trans-isomers and peak Nos. 2 and 4 are cis-isomers. The conditions used in determining the gas chromatogram of FIG. 1 are shown below.

Column: silicon OV-17, 2 m (dual)
Detector: FID detector
Initial temperature: 70° C., 4 minutes hold
Heating rate: 6° C/min.
Final temperature: 250° C., 16 minutes hold The process of the present invention is to selectively prepare perhydroacenaphthene isomers corresponding to Nos. 1 and 3 peaks in FIG. 1, that is, two trans-isomers.

Typical prior art methods for preparing a mixture of four isomers of perhydroacenaphthene are by subjecting acenaphthene to hydrogenation reaction in the presence of a catalyst under a hydrogen pressure of about 100 to 200 kg/cm² at a temperature of about 100° to 300° C. for several hours. Useful are catalysts comprising a carrier such as carbon and alumina having a noble metal such as Pd and Pt carried thereon and/or nickel-based catalysts such as Raney nickel.

Making a further study on the preparation of perhydroacenaphthene from acenaphthene with the aid of various hydrogenating catalysts, we have discovered that a particular perhydroacenaphthene can be produced in a high yield and a high selectivity by carrying out the hydrogenation reaction under certain conditions using a specific catalyst.

In order to preferentially produce perhydroacenaphthene isomers corresponding to Nos. 1 and 3 peaks in the gas chromatogram of FIG. 1, that is, the trans-isomers, it is recommended to hydrogenate acenaphthene under a hydrogen pressure of 100 to 200 kg/cm² gauge at a temperature of 200° to 300° C., more preferably 200° to 250° C. using a nickel catalyst on a kieselguhr or diatomeceous earth carrier.

The reaction can proceed at temperatures of lower than 200° C., but a mixture of four isomers comprising a major proportion of high boiling cis-isomers is produced at temperatures of about 150° to 180° C. At reaction temperatures of higher than 300° C., extraneous decomposition reaction takes place and control of reaction temperature is difficult. Preferably, reaction is effected at a temperature of 200° to 250° C. for a longer time.

The catalysts used herein are those comprising nickel carried on kieselguhr. Such nickel catalysts as Raney nickel catalysts are inadequate. A sufficient reaction rate is accomplished when the amount of the catalyst charged is at least 0.5% by weight based on the weight of acenaphthene.

The reaction time generally ranges from about 3 to about 10 hours although it varies with the catalyst charge and the reaction temperature. A shorter reaction time will result in a mixture of four isomers.

EXAMPLES

Examples of the present invention are presented below by way of illustration and not by way of limitation. All percents are by weight unless otherwise stated. Nos. 1 to 4 isomers are identified in the gas chromatogram of FIG. 1.

EXAMPLE 1

A shaking autoclave having an internal volume of about 60 ml was charged with 5 grams of acenaphthene and 0.2 gram of a 50% Ni/kieselguhr catalyst and with hydrogen at an initial pressure of 200 kg/cm$^2$ gauge. Reaction was effected at 200° C. for 7 hours. Perhydroacenaphthene was produced in a yield of 100%, and the combined selectivity of Nos. 1 and 3 trans-isomers was 96%.

EXAMPLE 2

Acenaphthene was hydrogenated by the same procedure as in Example 1 except that the reaction temperature was 250° C. Perhydroacenaphthene was produced in a yield of 100%, and the combined selectivity of Nos. 1 and 3 trans-isomers was 95.3%.

COMPARATIVE EXAMPLES

Acenaphthene was hydrogenated by the same procedure as in Example 1 except that the catalyst was replaced by a Raney nickel catalyst. Perhydroacenaphthene was produced in a yield of 100%, but the yields of Nos. 1 to 4 isomers were 18.9%, 8.3%, 37.4%, and 35.4%, respectively.

In another run, acenaphthene was hydrogenated in the presence of a 10% Pd/C catalyst at a temperature of 160° C. for a time of 6 hours. The yields of Nos. 1 to 4 isomers were 33.5%, 11.8%, 24.5%, and 29.7%, respectively.

In producing perhydroacenaphthene by hydrogenating acenaphthene, the process of the present invention can successfully produce perhydroacenaphthene in high yields and selectively obtain the two trans-isomers by employing a proper catalyst and reaction conditions.

Perhydroacenaphthene is used not only as high boiling oil and traction drive oil, but also as an intermediate for the production of adamantanes. In the latter case, the possible selective preparation of particular isomers in high yields according to the present invention offers a very useful reaction intermediate which ensures efficient synthesis of the destined product without incurring any variation in reaction route, activating energy and reaction yield.

We claim:

1. A process for selectively preparing trans-perhydroacenaphthene by hydrogenating acenaphthene, comprising hydrogenating acenaphthene at a temperature of 200° to 300° C. in the presence of a catalyst comprising nickel carried on kieselguhr, for a time sufficient to produce a product having a substantial majority of trans isomers of perhydroacenaphthene.

2. The process of claim 1 wherein the reaction temperature ranges from 200° to 250° C.

3. The process of claim 1 wherein the reaction is effected under a hydrogen pressure of 100 to 200 kg/cm$^2$.

4. The process of claim 1 wherein said reaction time is about 3 to 10 hours.

5. The process of claim 1 wherein said catalyst is present in an amount of at least 0.5% based on the weight of acenaphthene.

* * * * *